(12) United States Patent
Liu et al.

(10) Patent No.: US 9,301,693 B2
(45) Date of Patent: Apr. 5, 2016

(54) METHOD AND SYSTEM FOR IN-VIVO TEMPERATURE MEASUREMENT BASED ON AC MAGNETIZATION OF MAGNETIC NANOPARTICLE

(71) Applicant: Huazhong University of Science and Technology, Wuhan (CN)

(72) Inventors: Wenzhong Liu, Wuhan (CN); Jing Zhong, Wuhan (CN); Le He, Wuhan (CN); Ling Jiang, Wuhan (CN); Pu Zhang, Wuhan (CN)

(73) Assignee: HUAZHONG UNIVERSITY OF SCIENCE AND TECHNOLOGY (CN)

( * ) Notice: Subject to any disclaimer, the term of this patent is extended or adjusted under 35 U.S.C. 154(b) by 0 days.

(21) Appl. No.: 14/232,600

(22) PCT Filed: Jun. 25, 2013

(86) PCT No.: PCT/CN2013/077917
§ 371 (c)(1),
(2) Date: Jan. 13, 2014

(87) PCT Pub. No.: WO2014/131256
PCT Pub. Date: Sep. 4, 2014

(65) Prior Publication Data
US 2015/0045691 A1    Feb. 12, 2015

(30) Foreign Application Priority Data
Mar. 1, 2013   (CN) .......................... 2013 1 00658967

(51) Int. Cl.
*A61B 5/01* (2006.01)
*G01K 7/36* (2006.01)
(Continued)

(52) U.S. Cl.
CPC .................. *A61B 5/01* (2013.01); *A61B 5/0515* (2013.01); *G01K 7/36* (2013.01); *G01K 13/002* (2013.01); *G06F 17/16* (2013.01)

(58) Field of Classification Search
CPC .......................... A61B 2019/5454; A61B 5/01
See application file for complete search history.

(56) References Cited

U.S. PATENT DOCUMENTS 4,136,683 A    1/1979   Gordon
8,108,030 B2 *  1/2012   Castella et al. ............... 600/474
(Continued)

FOREIGN PATENT DOCUMENTS

CN    101918803    12/2010
CN    102156006    8/2011
CN    103156581    6/2013

OTHER PUBLICATIONS

X. Michalet, Quantum Dots for Live Cells, in Vivo Imaging, and Diagnostics, Feb. 14, 2015, Science Mag.*
(Continued)

*Primary Examiner* — Sean Dougherty
(74) *Attorney, Agent, or Firm* — Wenhua Yu (57) ABSTRACT

The invention discloses a method for in-vivo temperature measurement based on AC magnetization of magnetic nanoparticles, and relates to a nano test technology field. The invention positions magnetic nano agent at an area of a measured object, applies an AC excitation magnetic field to the area of the magnetic nano agent, collects an AC magnetization signal of the magnetic nano agent under the AC excitation magnetic field, detects amplitudes of odd harmonics of the AC magnetization signal, and finally calculates in-vivo temperature according to a relationship between the odd harmonics and the in-vivo temperature. The invention predetermines the relationship between the odd harmonics and the in-vivo temperature via the discrete Langevin's function and the Fourier transformation, solves the in-vivo temperature according to the relationship without considering concentration of the magnetic nanoparticles, and effective moment as temperature varies, and thus accurately detecting the in-vivo temperature.

10 Claims, 7 Drawing Sheets

(51) Int. Cl.
*A61B 5/05* (2006.01)
*G01K 13/00* (2006.01)
*G06F 17/16* (2006.01)

(56) References Cited

U.S. PATENT DOCUMENTS

2006/0020312 A1    1/2006   Eggers et al.
2011/0098558 A1    4/2011   Weaver et al.

OTHER PUBLICATIONS

Shuang Fang Lim, In Vivo and Scanning Electron Microscopy Imaging of Upconverting Nanophosphors in Caenorhabditis elegans, 2006, Nano Letters, vol. 6, No. 2, 169-174.*
Zhong J. et al. "Real-time magnetic nanothermometry: The use of magnetization of magnetic nanoparticles assessed under low frequency triangle-wave magnetic fields." *Review of Scientific Instruments* 85, 094905 (2014); doi: 10.1063/1.4896121.
Zhong J. et al. "A new approach for highly accurate, remote temperature probing using magnetic nanoparticles." *Scientific Reports* 4 : 6338 (2014); DOI: 10.1038/srep06338.
PCT International Search Report for PCT/CN2013/077917 filed Jun. 25, 2013 in the name of Huazhong University of Science and Technology.
PCT Written Opinion for PCT/CN2013/077917 filed Jun. 25, 2013 in the name of Huazhong University of Science and Technology.
English translation of PCT Written Opinion for PCT/CN2013/077917 filed Jun. 25, 2013 in the name of Huazhong University of Science and Technology.
Lu et al., "Linear and Shift Invariance of Magnetic Particle Imaging," T.M. Buzug and J. Borgert (Eds.): Magnetic Particle Imaging, SPPHY 140, pp. 155-160. Springer-Verlag Berlin Heidelberg 2012.
Graeser et al., "Analog receive signal processing for magnetic particle imaging," Medical Physics 40, 042303 (2013); doi: 10.1118/1.4794482.
Rauwerdin et al., "Nanoparticle temperature estimation in combined ac and dc magnetic fields," Phys. Med. Biol. 54 (2009) L51-L55.
Weaver et al., "Magnetic nanoparticle temperature estimation," Medical Physics, vol. 36, No. 5, May 2009, 1822-1829.

* cited by examiner

METHOD AND SYSTEM FOR IN-VIVO TEMPERATURE MEASUREMENT BASED ON AC MAGNETIZATION OF MAGNETIC NANOPARTICLE

CROSS REFERENCE TO RELATED APPLICATIONS

The present application is the US national stage of International Application PCT/CN2013/077917 filed on Jun. 25, 2013 which, in turn, claims priority to Chinese Patent Application CN2013100658967 filed on Mar. 1, 2013.

FIELD OF THE INVENTION

The invention relates to a nano test technology field, and more particularly to a method and a system for in-vivo temperature measurement based on AC magnetization of magnetic nanoparticles.

BACKGROUND OF THE INVENTION

In-vivo temperature refers to temperature of tissues in complete and survival individuals. In the biological and medical field, in-vivo temperature measurement methods are divided into invasive measurement and noninvasive measurement. The invasive measurement method is simple, real-time and accurate, and it is convenient to monitor measurement positions by videos. However, problems with the method are that, wound caused by the method is comparatively large, insertion of probes often leads to metastasis of pathological cells, interaction between radiation fields of heating sources and the probes reduces measurement accuracy, and measured temperature is temperature at a certain point, not temperature distribution over a whole coagulation area. The noninvasive temperature measurement method is now widely accepted and used in the medical field as being capable of effectively preventing infection of wound or expansion of cancer cell, and of providing real-time information of in-vivo temperature and temperature (field) distribution images deeply in tissues with comparatively high accuracy.

Presently, the noninvasive temperature measurement method comprises a ultrasound temperature measurement method, a microwave temperature measurement method, a nuclear magnetic resonance (NMR) temperature measurement method, a remote magnetic nanoparticle measurement method and so on.

Limited by size of organisms, the ultrasound temperature measurement method employs reflection echo, and a disadvantages thereof is that it must measure sound and temperature characteristics of different tissues in advance, but temperature characteristics of the tissues is significantly different and unstable. The microwave temperature measurement method can only be used to tumor at superficial layers, and resolution is to be significantly reduced at deep layers. However, this method must predetermine temperature distribution and measure structure and electrical parameters of organisms, this is because that thermal noise microwave measured at body surface is related to temperature distribution, structure of tissues and electrical properties within a measurement range. Problems with the NMR temperature measurement method are that it is too expensive to be widely used, spatial and temperature resolution thereof are limited, and more importantly, it can only obtain variation in temperature, not absolute temperature of tissues. A remote noninvasive temperature measurement method using magnetic nanoparticles is a high-accuracy temperature (field) measurement technique deeply in tissues being capable of addressing the above-mentioned problems. This method implements measurement and control of in-vivo temperature, and thus being capable of assessing and adjusting hyperthermia treatment of tumor in real time at a molecular level. In addition, a magnetic particle imaging (MPI) based on magnetic nanoparticles features an extremely high real-time rate in remote noninvasive in-vivo temperature measurement. Superior to a traditional noninvasive method for in-vivo temperature measurement—NMR, the MPI system is more simple, cost-effective and accurate, and generates pixels by changing magnetization of the magnetic nanoparticles whereby enabling the system to have high temperature sensibility. Therefore, the MPI is capable of measuring and imaging the in-vivo temperature in theory.

Temperature-related attributes of the magnetic nanoparticle comprise a particle size, saturated magnetic moment, concentration distribution thereof in the organism, and so on. The particle size and the saturated magnetic moment can be determined via repeated test outside the organism, but it is difficult to measure concentration of the magnetic nanoparticle in the organism, and no measurement method is available at present. Meanwhile, uncertainty of concentration and spatial distribution of the magnetic nanoparticle in the organism is to cause a significant error in the in-vivo temperature measurement. To summarize, to facilitate remote temperature measurement without knowing concentration of the magnetic nanoparticle has become an unsolved problem in magnetic nano hyperthermia treatment of tumor.

SUMMARY OF THE INVENTION

In view of the above-mentioned problems, it is an objective of the invention to provide a method for in-vivo temperature measurement based on AC magnetization of magnetic nanoparticles that is capable of accurately measuring in-vivo temperature without obtaining concentration of the magnetic nanoparticles.

A method for in-vivo temperature measurement, comprising steps of:

(1) positioning magnetic nano agent at an area of a measured object;

(2) applying an AC excitation magnetic field to the area of the magnetic nano agent;

(3) collecting an AC magnetization signal of the magnetic nano agent under the AC excitation magnetic field;

(4) detecting amplitudes $C_1, C_3, \ldots, C_{2n-1}$ of odd harmonics of the AC magnetization signal, the number of odd harmonics $n \geq 1$; and (5) calculating in-vivo temperature T according to a relationship between the odd harmonics and the in-vivo temperature X=AY, where the amplitudes of the odd harmonics form a column vector $$X = \begin{bmatrix} C_1 \\ C_3 \\ \vdots \\ C_{2n-1} \end{bmatrix};$$

a coefficient matrix A is defined as: the AC magnetization signal is expressed via the Langevin's function, and expression of the amplitudes of the odd harmonics is deduced from a Taylor series expansion of the Langevin's function, and thus the coefficient matrix $$A = \begin{bmatrix} \frac{M_s^2 H_0}{a_{1,1}k} & \frac{M_s^4 H_0^3}{a_{1,2}k^3} & \frac{M_s^6 H_0^5}{a_{1,3}k^5} & \cdots & \frac{M_s^{2m} H_0^{2m-1}}{a_{1,m}k^{2m-1}} \\ 0 & \frac{M_s^4 H_0^3}{a_{2,2}k^3} & \frac{M_s^6 H_0^5}{a_{2,3}k^5} & \cdots & \frac{M_s^{2m} H_0^{2m-1}}{a_{2,m}k^{2m-1}} \\ \vdots & \ddots & \ddots & \ddots & \vdots \\ \vdots & (0) & \ddots & \ddots & \frac{M_s^{2m} H_0^{2m-1}}{a_{n-1,m}k^{2m-1}} \\ 0 & \cdots & \cdots & \ddots & \frac{M_s^{2m} H_0^{2m-1}}{a_{n,m}k^{2m-1}} \end{bmatrix},$$

where $M_s$ is effective magnetic moment of a magnetic nanoparticle, k is a Boltzmann's constant, $H_0$ is an amplitude of the AC excitation magnetic field, $a_{u,v}$ is a coefficient of an element at the uth row and the vth column of the coefficient matrix A, u=1, 2, ..., n, v=1, 2 ..., m, m is the number of Taylor's expansion terms, and m≥n;

a related column vector Y of the in-vivo temperature is expressed as $$Y = \begin{bmatrix} \frac{N}{T} \\ \frac{N}{T^3} \\ \vdots \\ \frac{N}{T^{2n-1}} \end{bmatrix},$$

where T is the in-vivo temperature of the measured object, and N is magnetic nano concentration at the measured object.

Advantageously, as the number of the Taylor's expansion terms m is equal to the number of the odd harmonics n, step (5) comprises: calculating the related column vector of the in-vivo temperature $Y=A^{-1}x$, and further the in-vivo temperature $T=^{2(q-p)}\sqrt{Y_p/Y_q}$, 1≤p<q≤2n−1, where $Y_p$ and $Y_q$ respectively represents the $p^{th}$ and the $q^{th}$ element of the related column vector Y of the in-vivo temperature; and as the number of the Taylor's expansion terms m is greater than the number of the odd harmonics n, step (5) comprises: performing least square fitting via $B=[N,T]^T$ as a variable and the relationship between the odd harmonics and the in-vivo temperature X=AY as an objective function whereby determining the in-vivo temperature T.

Advantageously, step (4) uses a digital phase-sensitive detection method to detect the amplitudes of the odd harmonics, and comprises sub-steps of:

(a) sampling the AC magnetization signal M of the magnetic nano agent to obtain a discrete intensity signal M (i), where i=1, 2 ..., L, and L is the number of sampling points;

(b) setting j=1;

(c) calculating f'=(2j−1)f, where f is a frequency of the AC excitation magnetic field;

(d) generating two orthogonal reference signals, and sampling the orthogonal reference signals to obtain two discrete sampling signals $R_1(i)$ and $R_2(i)$;

(e) determining whether j is equal to 1, proceeding to step (g) if yes, and proceeding to step (f) otherwise;

(f) filtering the 2j−3$^{th}$ odd harmonic in the discrete intensity signal M(i);

(g) performing mutual correlation calculation and mean filtering on the discrete sampling signal $R_1(i)$ and the discrete intensity signal M(i) to obtain a first component $S_{2j-1}$, performing mutual correlation calculation and mean filtering on the discrete sampling signal $R_2(i)$ and the discrete intensity signal M(i) to obtain a second component $O_{2j-1}$, and calculating an amplitude of a 2j-1$^{th}$ odd harmonic $C_{2j-1}=2\sqrt{S_{2j-1}^2+O_{2j-1}^2}$; and (h) determining whether j is less than n, setting j=j+1 and retuning step (c) if yes, and ending otherwise.

Advantageously, step (4) uses a least square system parameter identification method to detect the amplitudes of the odd harmonics, and comprises sub-steps of:

sampling the AC magnetization signal M of the magnetic nano agent to obtain a discrete intensity signal M(i), where i=1, 2 . . . , L, and L is the number of sampling points;

assuming $$Z = \begin{bmatrix} M(1) \\ M(2) \\ \vdots \\ M(L) \end{bmatrix} \text{ and } \varphi = \begin{bmatrix} \sin(\Omega) & \sin(3\Omega) & \cdots & \sin((2n-1)\Omega) \\ \sin(2\Omega) & \sin(6\Omega) & \cdots & \sin(2(2n-1)\Omega) \\ \vdots & \vdots & \ddots & \vdots \\ \sin(L\Omega) & \sin(3L\Omega) & \cdots & \sin(L(2n-1)\Omega) \end{bmatrix},$$

finding matrices ϕ and Z so that $J=[Z-\phi X]^T[Z-\phi X]$ is the minimum by adjusting a sampling frequency, and determining the column vector $X=(\phi^T\phi)^{-1}\phi^T Z$ formed by the amplitudes $C_j$ of the odd harmonics, where a digital angular frequency $$\Omega = \frac{2\pi f}{f_s},$$

$f_s$ represents a sampling frequency, π represents a circumference ratio, and a superscript T represents transpose.

Advantageously, intensity of the AC excitation magnetic field ranges from 20 Oe to 1000 Oe, and a frequency of the AC excitation magnetic field ranges from 20 Hz to 20 kHz.

Advantageously, the number of the odd harmonics ranges from 2 to 4, and that of the Taylor's expansion terms m ranges from 2 to 6.

It is another objective of the invention to provide a method for in-vivo temperature measurement based on AC magnetization of magnetic nanoparticles that is capable of accurately measuring in-vivo temperature without obtaining concentration of the magnetic nanoparticles.

An in-vivo temperature measurement system, comprising:

a first module configured to position magnetic nano agent at an area of a measured object;

a second module configured to apply an AC excitation magnetic field to the area of the magnetic nano agent;

a third module configured to collect an AC magnetization signal of the magnetic nano agent under the AC excitation magnetic field;

a fourth module configured to detect amplitudes $C_1$, $C_3$, . . . , $C_{2n-1}$ of odd harmonics of the AC magnetization signal, the number of odd harmonics n 1; and a fifth module configured to calculate in-vivo temperature T according to a relationship between the odd harmonics and the in-vivo temperature X=AY, where the amplitudes of the odd harmonics form a column vector $$X = \begin{bmatrix} C_1 \\ C_3 \\ \vdots \\ C_{2n-1} \end{bmatrix};$$

a coefficient matrix A is defined as: the AC magnetization signal is expressed via the Langevin's function, and expression of the amplitudes of the odd harmonics is deduced from a Taylor series expansion of the Langevin's function, and thus the coefficient matrix $$A = \begin{bmatrix} \frac{M_s^2 H_0}{a_{1,1}k} & \frac{M_s^4 H_0^3}{a_{1,2}k^3} & \frac{M_s^6 H_0^5}{a_{1,3}k^5} & \cdots & \frac{M_s^{2m} H_0^{2m-1}}{a_{1,m}k^{2m-1}} \\ 0 & \frac{M_s^4 H_0^3}{a_{2,2}k^3} & \frac{M_s^6 H_0^5}{a_{2,3}k^5} & \cdots & \frac{M_s^{2m} H_0^{2m-1}}{a_{2,m}k^{2m-1}} \\ \vdots & \ddots & \ddots & \ddots & \vdots \\ \vdots & (0) & \ddots & \ddots & \frac{M_s^{2m} H_0^{2m-1}}{a_{n-1,m}k^{2m-1}} \\ 0 & \cdots & \cdots & \ddots & \frac{M_s^{2m} H_0^{2m-1}}{a_{n,m}k^{2m-1}} \end{bmatrix},$$

where $M_s$ is effective magnetic moment of a magnetic nanoparticle, k is a Boltzmann's constant, $H_0$ is an amplitude of the AC excitation magnetic field, $a_{u,v}$ is a coefficient of an element at the uth row and the vth column of the coefficient matrix A, $u=1, 2, \ldots, n$, $v=1, 2 \ldots, m$, m is the number of Taylor's expansion terms, and $m \geq n$;

a related column vector Y of the in-vivo temperature is expressed as $$Y = \begin{bmatrix} \frac{N}{T} \\ \frac{N}{T^3} \\ \vdots \\ \frac{N}{T^{2m-1}} \end{bmatrix},$$

where T is the in-vivo temperature of the measured object, and N is magnetic nano concentration at the measured object.

Advantageously, the fifth module comprises:

a fifty-first sub-module configured to calculate the related column vector of the in-vivo temperature $Y=A^{-1} X$, and further the in-vivo temperature $T=2(q-p)\sqrt{Y_p/Y_q}$, $1 \leq p < q \leq 2n-1$ as the number of the Taylor's expansion terms m is equal to the number of the odd harmonics n, where $Y_p$ and $Y_q$ respectively represents the $p^{th}$ and the $q^{th}$ element of the related column vector Y of the in-vivo temperature; and a fifty-second sub-module configured to perform least square fitting via $B=[N,T]^T$ as a variable and the relationship between the odd harmonics and the in-vivo temperature $X=AY$ as an objective function whereby determining the in-vivo temperature T as the number of the Taylor's expansion terms m is greater than the number of the odd harmonics n.

Advantageously, the fourth module uses a digital phase-sensitive detection method to detect the amplitudes of the odd harmonics, and comprises:

a forty-first sub-module configured to sample the AC magnetization signal M of the magnetic nano agent to obtain a discrete intensity signal M(i), where $i=1, 2 \ldots, L$, and L is the number of sampling points;

a forty-second sub-module configured to set $j=1$;

a forty-third sub-module configured to calculate $f'=(2j-1)f$, where f is a frequency of the AC excitation magnetic field;

a forty-fourth sub-module configured to generate two orthogonal reference signals, and to sample the orthogonal reference signals to obtain two discrete sampling signals $R_1(i)$ and $R_2(i)$;

a forty-fifth sub-module configured to determine whether j is equal to 1, to proceed to step (g) if yes, and to proceed to step (f) otherwise;

a forty-sixth sub-module configured to filter the $2j-3^{th}$ odd harmonic in the discrete intensity signal M(i);

a forty-seventh sub-module configured to perform mutual correlation calculation and mean filtering on the discrete sampling signal $R_1(i)$ and the discrete intensity signal M (i) to obtain a first component $S_{2j-1}$, to perform mutual correlation calculation and mean filtering on the discrete sampling signal $R_2(i)$ and the discrete intensity signal M (i) to obtain a second component $O_{2j-1}$, and to calculate an amplitude of a $2j-1^{th}$ odd harmonic $C_{2j-1}=2\sqrt{S_{2j-1}^2+O_{2j-1}^2}$; and a forty-eighth sub-module configured to determine whether j is less than n, to set $j=j+1$ and return step (c) if yes, and to end otherwise.

Advantageously, the fourth module uses a least square system parameter identification method to detect the amplitudes of the odd harmonics, the fourth module is configured to sample the AC magnetization signal M of the magnetic nano agent to obtain a discrete intensity signal M(i), where $i=1, 2 \ldots, L$, and L is the number of sampling points;

assuming $$Z = \begin{bmatrix} M(1) \\ M(2) \\ \vdots \\ M(L) \end{bmatrix} \text{ and } \varphi = \begin{bmatrix} \sin(\Omega) & \sin(3\Omega) & \cdots & \sin((2n-1)\Omega) \\ \sin(2\Omega) & \sin(6\Omega) & \cdots & \sin(2(2n-1)\Omega) \\ \vdots & \vdots & \ddots & \vdots \\ \sin(L\Omega) & \sin(3L\Omega) & \cdots & \sin(L(2n-1)\Omega) \end{bmatrix},$$

to find matrices $\varphi$ and Z so that $J=[Z-\varphi X]^T[Z-\varphi X]$ is the minimum by adjusting a sampling frequency, and to determine the column vector $X=(\varphi^T\varphi)^{-1}\varphi^T Z$ formed by the amplitudes $C_j$ of the odd harmonics, where a digital angular frequency $$\Omega = \frac{2\pi f}{f_s},$$

$f_s$ represents a sampling frequency, $\pi$ represents a circumference ratio, and a superscript T represents transpose.

Advantages of the Invention Comprise:

The invention applies the AC excitation magnetic field to the field of the magnetic nano agent, collects the AC magnetization of the magnetic nano agent under the AC excitation magnetic field, detects the odd harmonics of the AC magnetization signal of the magnetic nanoparticles, analyzes spectrum information of a magnetic intensity model of the magnetic nanoparticles via the discrete Langevin's function and the Fourier transformation, establishes a matrix relationship between the odd harmonics and temperature and concentration of the magnetic nanoparticles, and solves the in-vivo temperature according to the relationship without considering concentration of the magnetic nanoparticles, and effective moment as temperature varies, and thus accurately detecting the in-vivo temperature. In addition, the invention is capable of accurately and rapidly detecting the in-vivo temperature, and is especially applicable to detect thermal motion of biological molecules, and an average error thereof after ten times of measurement experiments at a SNR of 80 dB is less than 0.2K.

SPECIFIC EMBODIMENT OF THE INVENTION

For clear understanding of the objectives, features and advantages of the invention, detailed description of the invention will be given below in conjunction with accompanying drawings and specific embodiments. It should be noted that the embodiments are only meant to explain the invention, and not to limit the scope of the invention.

Figure 1:
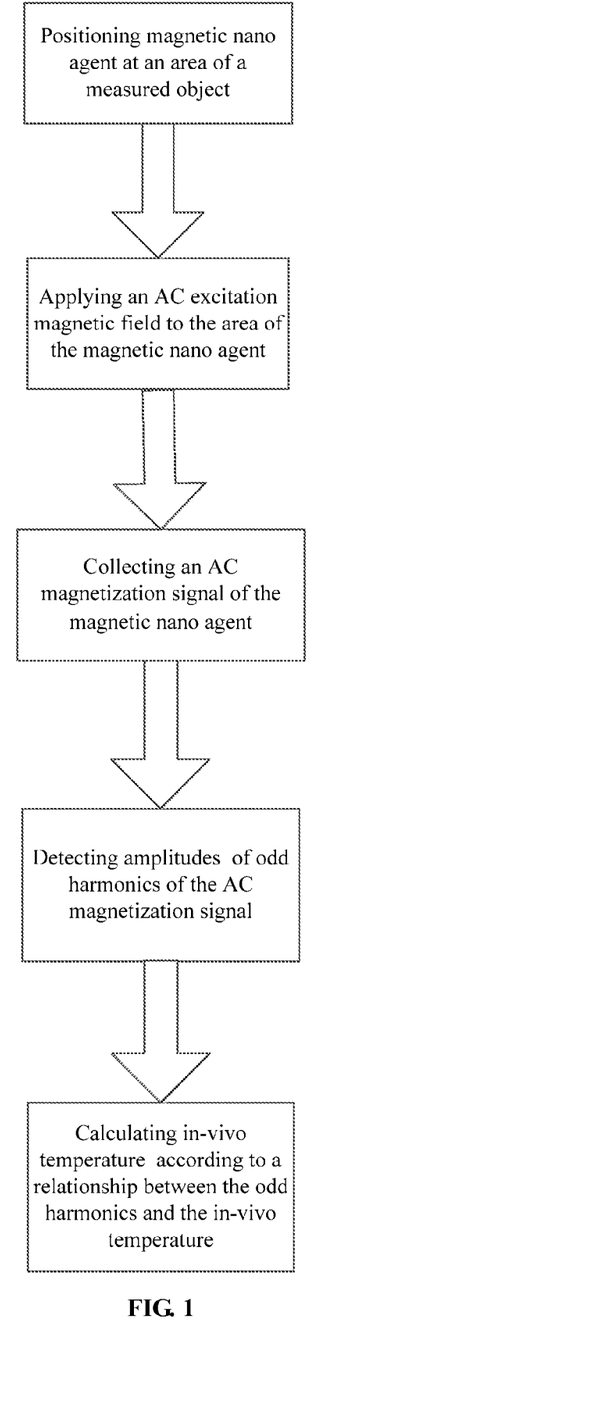
FIG. 1 is a flowchart of a method for in-vivo temperature measurement of an exemplary embodiment of the invention.

As shown in FIG. 1, a method for in-vivo temperature measurement of the invention comprises steps of:

(1) positioning magnetic nano agent at an area of a measured object;

in details, firstly surface of magnetic nanoparticles is covered with modification agent, and then the magnetic nanoparticles are redirected to the measured objects, such as various biological organs, along with blood circulation systems via injection.

(2) applying an AC excitation magnetic field to the area of the magnetic nano agent;

Using a Taylor series expansion of the Langevin's function of magnetization to calculate amplitudes of odd harmonics in the following steps is based on a weak excitation magnetic field, but a too weak excitation magnetic field is to lead to a small SNR of the magnetization, and make it difficult to extract high harmonics. Therefore, it is very important to select an appropriate strength for the AC excitation magnetic field, normally 20~1000 Oe, and advantageously 100 Oe. In addition, a frequency of the AC excitation magnetic field is 20 Hz to 20 kHz, and advantageously 1 kHz.

(3) collecting an AC magnetization signal of the magnetic nano agent under the AC excitation magnetic field;

a detection coil as a sensor is placed in the vicinity of the measured object containing the magnetic nano agent, magnetization analog signal induced thereby is pre-processed by a conditioning circuit, and then sampled and transmitted to a computer for further procession via a data acquisition card.

(4) detecting amplitudes of odd harmonics of the AC magnetization signal;

firstly, the AC magnetization signal is modeled: AC magnetization of magnetic nanoparticles with paramagnetic characteristics follows the Langevin's function as follows:

$$M = NM_s\left[\coth\left(\frac{M_s H}{kT}\right) - \frac{kT}{M_s H}\right] = NM_s L\left(\frac{M_s H}{kT}\right)$$

where $$L\left(\frac{M_s H}{kT}\right)$$

is the Langevin's function, N is concentration of the magnetic nano agent, the excitation magnetic field $H=H_0 \sin(2\pi ft)$, $H_0$ is a amplitude of the excitation magnetic field, f is a frequency of the excitation magnetic field, $M_s$ is effective magnetic moment of the magnetic nanoparticle, k is the Boltzmann's constant, T is temperature of the magnetic nanoparticle, namely in-vivo temperature of the measured object.

Then the above equation is divided into multiple frequency mixing signals containing multiple odd harmonics, namely $$M = \sum_{j=1}^{n} C_{2j-1}\sin(2j-1)\omega t, n \geq 1$$

where $C_{2j-1}$ is an amplitude of the $2j-1^{th}$ odd harmonic, an angular frequency $\omega=2\pi f$, t is time, n is the preset number of polynominal expansion terms that determines the number of all measured odd harmonics, if n is too small, an approximation error of finite terms of the AC magnetization and thus a temperature estimation error become large, if n is too large, it is difficult to accurately detect weak amplitude signals of high harmonics, and thus the temperature estimation error is to be increased. It is suggested that n range from 2 to 4.

By replacing the Fourier equation $$C_{2j-1} = \frac{1}{\pi}\int_{-\pi}^{\pi} M\sin((2j-1)\omega t)\,d\omega t$$

with the Taylor series expansions $$M = \frac{NM_s^2}{3kT}H - \frac{NM_s^4}{45k^3T^3}H^3 + \frac{2NM_s^6}{945k^5T^5}H^5 - \frac{NM_s^8}{4725k^7T^7}H^7 \ldots + \frac{NM_s^{2m}}{b_m k^{2m-1} T^{2m-1}}H^{2m-1},$$

it is possible to obtain an expression for an amplitude $C_{2j-1}$ of each harmonic, $b_m$ is a constant, the number of Taylor's expansion terms m ranges from 2 to 6, and m≥n An example in which the number of odd harmonics n=4 and the number of Taylor's expansion terms m=4 will be given below:

$$M = C_1\sin(\omega t) + C_3\sin(3\omega t) + C_5\sin(5\omega t) + C_7\sin(7\omega t),$$

where
$$\begin{cases} C_1 = \dfrac{NM_s^2 H_0}{3kT} - \dfrac{NM_s^4 H_0^3}{60k^3 T^3} + \dfrac{NM_s^6 H_0^5}{756k^5 T^5} - \dfrac{NM_s^8 H_0^7}{8640k^7 T^7} \\ C_3 = \dfrac{NM_s^4 H_0^3}{180k^3 T^3} - \dfrac{NM_s^6 H_0^5}{1512k^5 T^5} + \dfrac{NM_s^8 H_0^7}{14400k^7 T^7} \\ C_5 = \dfrac{NM_s^6 H_0^5}{7560k^5 T^5} - \dfrac{NM_s^8 H_0^7}{43200k^7 T^7} \\ C_7 = \dfrac{NM_s^8 H_0^7}{302400k^7 T^7} \end{cases},$$

the odd harmonics are proportional to concentration of the particles per unit volume, and harmonic ratios are functionally related to temperature and irrelevant to the concentration, and can prove approximation of the temperature without knowing particle concentration.

Based on the above model, this step employs a digital phase-sensitive detection (DPSD) method and a least square system parameter identification method to measure the amplitudes of the odd harmonics of different AC magnetization.

Measurement of an amplitude of a fundamental harmonic $C_1$, an amplitude of a third harmonic $C_3$, an amplitude of a fifth harmonic $C_5$, and an amplitude of a seventh harmonic $C_7$ of different AC magnetization using the DPSD and the least square system parameter identification method is described below with reference to an example in which the number of the harmonics n=4.

A. Using the DPSD to Measure the Amplitudes of the Odd Harmonics

Figure 2:
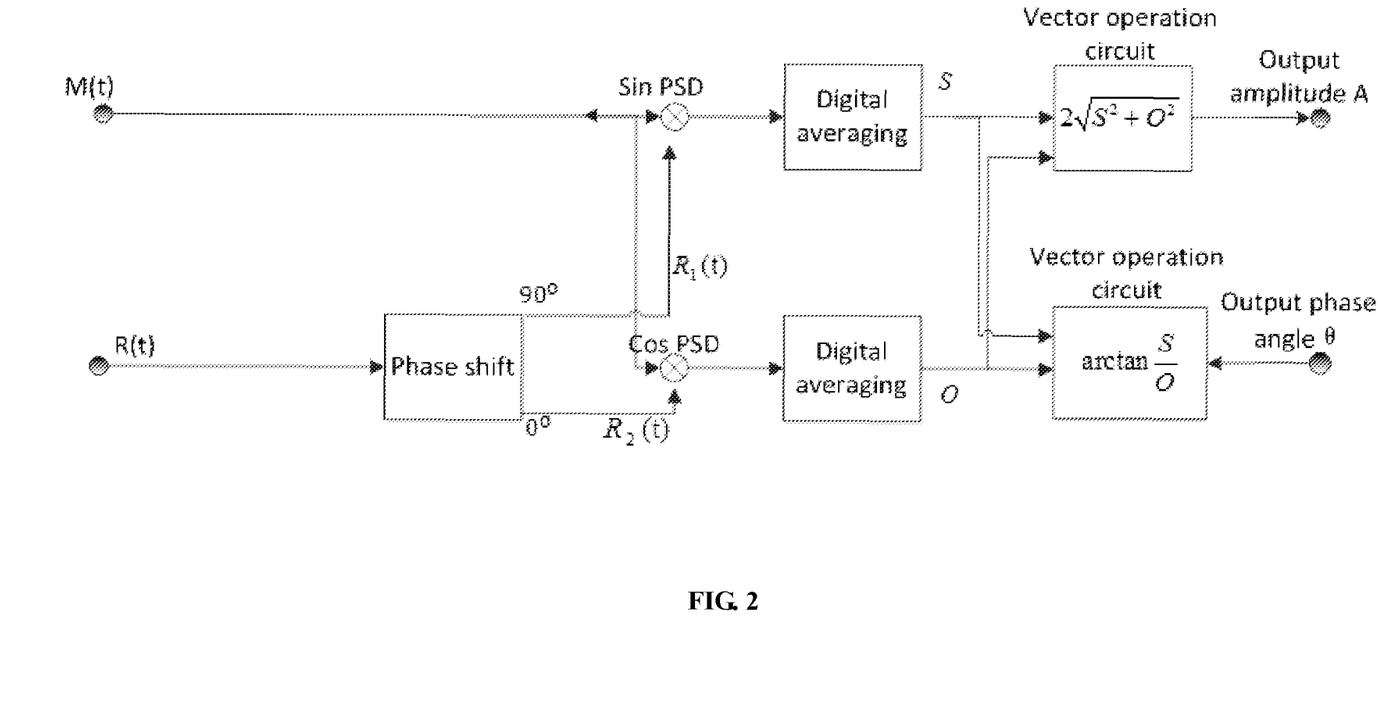
FIG. 2 illustrates principle of a digital phase-sensitive detection (DPSD) method.

FIG. 2 illustrates a principle of the DPSD. Firstly two orthogonal reference signals are set according to a particular frequency to be extracted f': $R_1(t)=\cos(2\pi f't)$, $R_2(t)=\sin(2\pi f't)$, and then respectively mutually correlated with a measured signal M(t), then mean-filtered whereby forming two components $$S = \frac{A}{2}\sin\theta \text{ and } O = \frac{A}{2}\cos\theta,$$

where A is a amplitude of the particular frequency, $\theta$ is a phase angle of the particular frequency, and finally the amplitude and the phase angle can be obtained according to equations $A=2\sqrt{S^2+O^2}$ and $$\theta = \arctan\frac{S}{O}.$$

Figure 3:
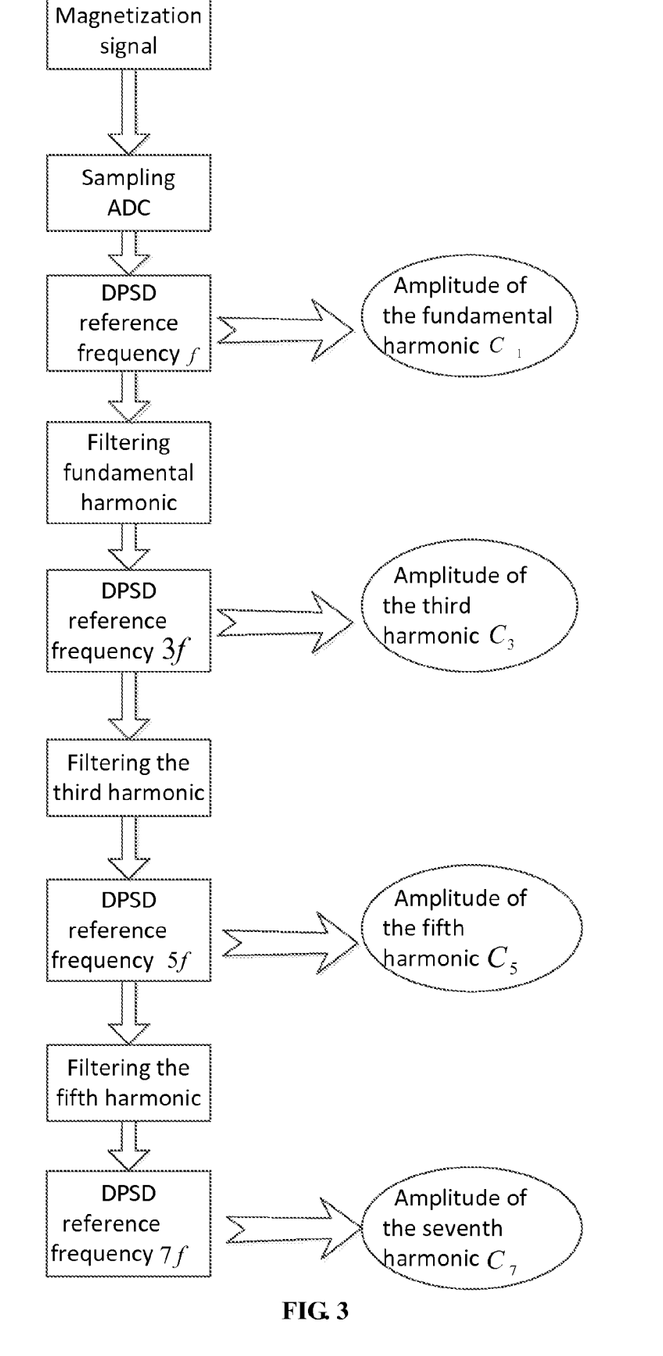
FIG. 3 illustrates measurement of different harmonics using the digital phase-sensitive detection method.

FIG. 3 illustrates measurement of different harmonics using the digital phase-sensitive detection method, and a detailed measurement process is as follows:

A1. Signal Sampling

The AC magnetization signal M of the magnetic nanoparticles is $M(i)=C_1\sin(\Omega i)+C_3\sin(3\Omega i)+C_5\sin(5\Omega i)+C_7\sin(7\Omega i)+\epsilon(i)$ after analog-digital conversion, and the two reference signals are $R_1(i)=\cos(\Omega' i)$, $R_2(i)=\sin(\Omega' i)$ after analog-digital conversion, where f is an excitation frequency, $f_s$ is a sampling frequency, a digital angular frequency $$\Omega = \frac{2\pi f}{f_s}, \quad \Omega' = \frac{2\pi f'}{f_s},$$

sampling points i=1, 2 ..., L, L is the length of discrete sampling series, $\epsilon(.)$ is an error function containing high harmonics.

A2. Extraction of Amplitudes of Harmonics (1) To obtain an amplitude of the fundamental harmonic, assume f'=f and use the DPSD method to get:

$$S_1 = \frac{1}{L}\sum_{i=1}^{L} M(i)R_1(i) = \frac{C_1}{2}\sin\theta$$

$$O_1 = \frac{1}{L}\sum_{i=1}^{L} M(i)R_2(i) = \frac{C_1}{2}\cos\theta$$

then the amplitude of the fundamental harmonic is $$C_1 = 2\sqrt{S_1^2 + O_1^2}$$

(2) after the amplitude $C_1$ of the fundamental harmonic is obtained, to obtain the amplitude $C_3$ of the third harmonic with high accuracy, assume f'=3 f and use the DPSD method to process a magnetization signal M' after filtering the fundamental harmonic and get:

$$S_3 = \frac{1}{L}\sum_{i=1}^{L} M'(i)R_1(i) = \frac{C_3}{2}\sin\theta$$

$$O_3 = \frac{1}{L}\sum_{i=1}^{L} M'(i)R_2(i) = \frac{C_3}{2}\cos\theta$$

then the amplitude of the third harmonic is $$C_3 = 2\sqrt{S_3^2 + O_3^2}$$

(3) after the amplitude $C_3$ of the third harmonic is obtained, for the magnetization M" after the third harmonic of M' is filtered, assume f'=5f and use the DPSD method to get:

$$S_5 = \frac{1}{L}\sum_{i=1}^{L} M''(i)R_1(i) = \frac{C_5}{2}\sin\theta$$

$$O_5 = \frac{1}{L}\sum_{i=1}^{L} M''(i)R_2(i) = \frac{C_5}{2}\cos\theta$$

then the amplitude of the fifth harmonic is $$C_5 = 2\sqrt{S_5^2 + O_5^2}$$

(4) after the amplitude $C_5$ of the fifth harmonic is obtained, for the magnetization M''' after the third harmonic of M" is filtered, assume f'=7 f and use the DPSD method to get:

$$S_7 = \frac{1}{L}\sum_{i=1}^{L} M'''(i)R_1(i) = \frac{C_7}{2}\sin\theta$$

-continued $$O_7 = \frac{1}{L}\sum_{i=1}^{L} M'''(i)R_2(i) = \frac{C_7}{2}\cos\theta$$

then the amplitude of the seventh harmonic is $$C_7 = 2\sqrt{S_7^2 + O_7^2}$$

By performing the above steps, it is possible to extract the amplitudes of the harmonics in the AC magnetization signal of the magnetic nanoparticles via the DPSD method.

Figure 4:
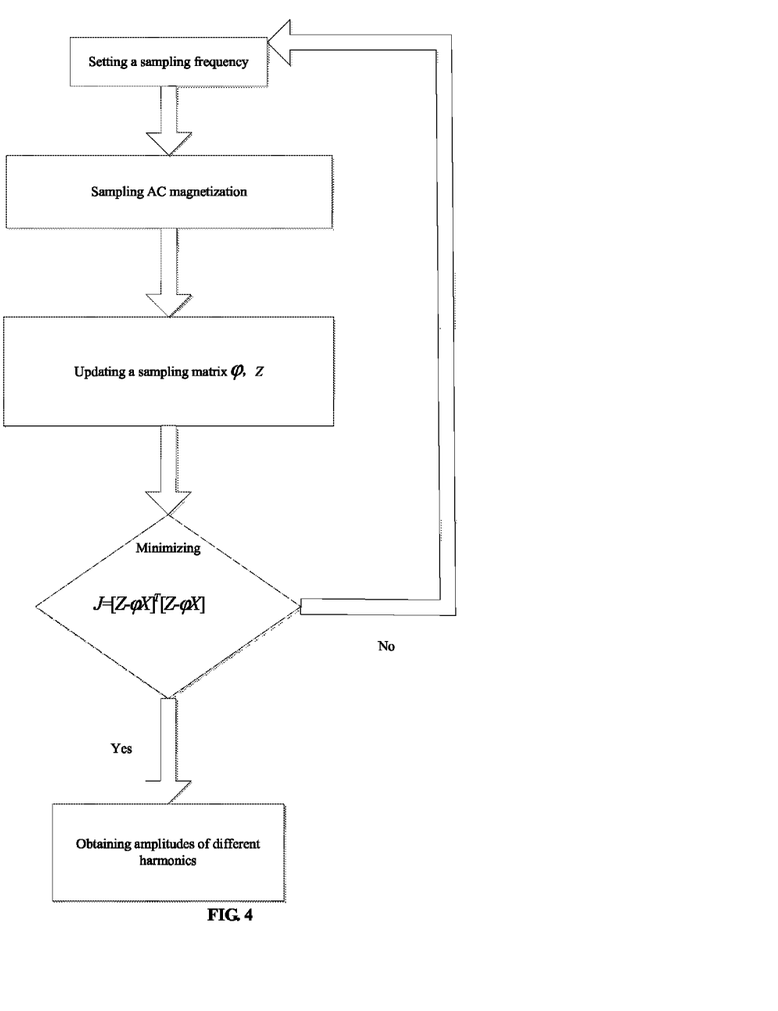
FIG. 4 illustrates measurement of different harmonics using a least square system parameter identification method.

B. Using the Least Square System Parameter Identification Method to Measure Harmonics FIG. 4 illustrates measurement of different harmonics using the least square system parameter identification method, and a detailed measurement process is as follows:

Signal sampling: The AC magnetization signal M of the magnetic nanoparticles is $M(i)=C_1 \sin(\Omega i)+C_3 \sin(3\Omega i)+C_5 \sin(5\Omega i)+C_7 \sin(7\Omega i)+\epsilon(i)$ after analog-digital conversion, where f is an excitation frequency, $f_s$ is a sampling frequency, a digital angular frequency $$\Omega = \frac{2\pi f}{f_s},$$

sampling points $i=1, 2 \ldots, L$, $\epsilon(.)$ is an error function containing high harmonics, and L is the length of discrete sampling series.

Then the above equation is further converted to a matrix relationship:

$$\begin{bmatrix} M(1) \\ M(2) \\ \vdots \\ M(L) \end{bmatrix} = \begin{bmatrix} \sin(\Omega) & \sin(3\Omega) & \sin(5\Omega) & \sin(7\Omega) \\ \sin(2\Omega) & \sin(6\Omega) & \sin(10\Omega) & \sin(14\Omega) \\ \vdots & \vdots & \vdots & \vdots \\ \sin(L\Omega) & \sin(3L\Omega) & \sin(5L\Omega) & \sin(7L\Omega) \end{bmatrix} \begin{bmatrix} C_1 \\ C_3 \\ C_5 \\ C_7 \end{bmatrix} + \begin{bmatrix} \varepsilon(1) \\ \varepsilon(2) \\ \vdots \\ \varepsilon(L) \end{bmatrix},$$

$$\text{assume } Z = \begin{bmatrix} M(1) \\ M(2) \\ \vdots \\ M(L) \end{bmatrix}, \varphi = \begin{bmatrix} \sin(\Omega) & \sin(3\Omega) & \sin(5\Omega) & \sin(7\Omega) \\ \sin(2\Omega) & \sin(6\Omega) & \sin(10\Omega) & \sin(14\Omega) \\ \vdots & \vdots & \vdots & \vdots \\ \sin(L\Omega) & \sin(3L\Omega) & \sin(5L\Omega) & \sin(7L\Omega) \end{bmatrix},$$

$$X = \begin{bmatrix} C_1 \\ C_3 \\ C_5 \\ C_7 \end{bmatrix}, e = \begin{bmatrix} \varepsilon(1) \\ \varepsilon(2) \\ \vdots \\ \varepsilon(L) \end{bmatrix}, \text{ then } Z = \varphi X + e, \text{ an error vector } e = Z - \varphi X.$$

In the model, the least square system parameter identification method assesses fitting of measurement data based on estimation of a unknown parameter vector X being capable of minimizing square sum of errors, namely $$J = \sum_{i=1}^{L} \varepsilon^2(i) = e^T e.$$

To minimize $J=[Z-\phi X]^T[Z-\phi X]$, it is required to find appropriate matrices $\phi$ and Z by adjusting a sampling frequency. Assume an optimum estimation column vector $\hat{X}=(\phi^T\phi)^{-1}\phi^T Z$, let $$\left.\frac{\partial J}{\partial \hat{X}}\right|_{X=\hat{X}} = 0,$$

namely J is the minimum. Thus, the amplitude of the fundamental harmonic $C_1$, the amplitude of the third harmonic $C_3$, the amplitude of the fifth harmonic $C_5$, and the amplitude of the seventh harmonic $C_7$ can be obtained from the optimum estimation column vector $\hat{X}$.

(5) calculating in-vivo temperature according to the matrix relationship between the amplitudes $C_{2j-1}$ of the odd harmonics and the in-vivo temperature T;

The amplitudes $C_{2j-1}$ of the odd harmonics and the in-vivo temperature T follow a matrix relationship X=AY, where X is a column vector formed by the amplitudes $C_{2j-1}$ of the odd harmonics, and $$X = \begin{bmatrix} C_1 \\ C_3 \\ \vdots \\ C_{2n-1} \end{bmatrix},$$

Y is a related column vector of the in-vivo temperature, and $$Y = \begin{bmatrix} \dfrac{N}{T} \\ \dfrac{N}{T^3} \\ \vdots \\ \dfrac{N}{T^{2m-1}} \end{bmatrix},$$

the coefficient matrix A is defined as: the AC magnetization signal is expressed via the Langevin's function, and expression of the amplitudes of the odd harmonics is deduced from a Taylor series expansion of the Langevin's function, and thus the coefficient matrix $$A = \begin{bmatrix} \dfrac{M_s^2 H_0}{a_{1,1}k} & \dfrac{M_s^4 H_0^3}{a_{1,2}k^3} & \dfrac{M_s^6 H_0^5}{a_{1,3}k^5} & \cdots & \dfrac{M_s^{2m}H_0^{2m-1}}{a_{1,m}k^{2m-1}} \\ 0 & \dfrac{M_s^4 H_0^3}{a_{2,2}k^3} & \dfrac{M_s^6 H_0^5}{a_{2,3}k^5} & \cdots & \dfrac{M_s^{2m}H_0^{2m-1}}{a_{2,m}k^{2m-1}} \\ \vdots & \ddots & \ddots & \ddots & \vdots \\ \vdots & (0) & \ddots & \ddots & \dfrac{M_s^{2m}H_0^{2m-1}}{a_{n-1,m}k^{2m-1}} \\ 0 & \cdots & \cdots & \ddots & \dfrac{M_s^{2m}H_0^{2m-1}}{a_{n,m}k^{2m-1}} \end{bmatrix},$$

where $a_{u,v}$ is a coefficient of an element at the uth row and the vth column of the coefficient matrix A, $u=1, 2, \ldots, n$, $v=1, 2 \ldots, m$, $m \geq n$.

Using the above relationship between the harmonics and the temperature X=AY to solve the in-vivo temperature comprises the following two scenarios:

(a) as the number of the Taylor's expansion terms m is equal to the number of the odd harmonics n, step (5) comprises: calculating the related column vector of the in-vivo temperature $Y=A^{-1} X$, and further the in-vivo temperature $T=^{2(q-p)}\sqrt{Y_p/Y_q}$, $1 \leq p<q \leq 2n-1$, where $Y_p$ and $Y_q$ respectively represents the $p^{th}$ and the $q^{th}$ element of the related column vector Y of the in-vivo temperature;

(b) as the number of the Taylor's expansion terms m is greater than the number of the odd harmonics n, step (5) comprises: performing least square fitting via $B=[N,T]^T$ as a variable and the relationship between the odd harmonics and the in-vivo temperature $X=AY$ as an objective function whereby determining the in-vivo temperature T.

An example in which m=n=4 is described as follows:

$$\begin{cases} C_1 = \frac{NM_s^2 H_0}{3kT} - \frac{NM_s^4 H_0^3}{60k^3 T^3} + \frac{NM_s^6 H_0^5}{756k^5 T^5} - \frac{NM_s^8 H_0^7}{8640k^7 T^7} \\ C_3 = \frac{NM_s^4 H_0^3}{180k^3 T^3} - \frac{NM_s^6 H_0^5}{1512k^5 T^5} + \frac{NM_s^8 H_0^7}{14400k^7 T^7} \\ C_5 = \frac{NM_s^6 H_0^5}{7560k^5 T^5} - \frac{NM_s^8 H_0^7}{43200k^7 T^7} \\ C_7 = \frac{NM_s^8 H_0^7}{302400k^7 T^7} \end{cases}$$

is converted to a matrix relationship:

$$\begin{bmatrix} C_1 \\ C_3 \\ C_5 \\ C_7 \end{bmatrix} = \begin{bmatrix} \frac{M_s^2 H_0}{3k} & -\frac{M_s^4 H_0^3}{60k^3} & \frac{M_s^6 H_0^5}{756k^5} & -\frac{M_s^8 H_0^7}{8640k^7} \\ 0 & \frac{M_s^4 H_0^3}{180k^3} & -\frac{M_s^6 H_0^5}{1512k^5} & \frac{M_s^8 H_0^7}{14400k^7} \\ 0 & 0 & \frac{M_s^6 H_0^5}{7560k^5} & -\frac{M_s^8 H_0^7}{43200k^7} \\ 0 & 0 & 0 & \frac{M_s^8 H_0^7}{302400k^7} \end{bmatrix} \begin{bmatrix} N \\ \frac{N}{T^3} \\ \frac{N}{T^5} \\ \frac{N}{T^7} \end{bmatrix},$$

assume a related column vector of the temperature $$T: Y = \begin{bmatrix} \frac{N}{T} \\ \frac{N}{T^3} \\ \frac{N}{T^5} \\ \frac{N}{T^7} \end{bmatrix},$$

the amplitudes of the odd harmonics form a column vector $$X = \begin{bmatrix} C_1 \\ C_3 \\ C_5 \\ C_7 \end{bmatrix},$$

coefficient matrix A is $$\begin{bmatrix} \frac{M_s^2 H_0}{3k} & -\frac{M_s^4 H_0^3}{60k^3} & \frac{M_s^6 H_0^5}{756k^5} & -\frac{M_s^8 H_0^7}{8640k^7} \\ 0 & \frac{M_s^4 H_0^3}{180k^3} & -\frac{M_s^6 H_0^5}{1512k^5} & \frac{M_s^8 H_0^7}{14400k^7} \\ 0 & 0 & \frac{M_s^6 H_0^5}{7560k^5} & -\frac{M_s^8 H_0^7}{43200k^7} \\ 0 & 0 & 0 & \frac{M_s^8 H_0^7}{302400k^7} \end{bmatrix}$$

then the related column vector of the in-vivo temperature is calculated $Y=A^{-1} X$, thus the temperature T can be measured by any two dimensional data (such as the $p^{th}$ dimension and the $q^{th}$ dimension) without knowing concentration of the magnetic nanoparticles, namely $$T = \sqrt[2(q-p)]{Y_p/Y_q} = \sqrt[2(q-p)]{\left(\frac{N}{T^{2p-1}}\right)/\left(\frac{N}{T^{2q-1}}\right)}, 1 \leq p < q \leq 4$$

where $Y_p$ and $Y_q$ respectively represents the $p^{th}$ and the $q^{th}$ element of the related column vector Y of the in-vivo temperature. Advantageously, as P=1, q=2, highly accurate results can be obtained.

Simulation Example

1. Simulation Model and Test Description

To study effectiveness of the temperature measurement method and to optimize design, the example uses simulation data with noise to test the algorithm of the invention. During simulation and testing, effective moment $M_s$ of the particles in the agent is $4\times10^{-19}$ (the value is determined by the type of the agent). Since a quadrinomial approximation model of the Fourier series of the AC magnetization causes error effect, an AC excitation magnetic field with a small amplitude must be used. In this example, the amplitude of the AC excitation magnetic field $H_0$=100 Oe. A noise model uses a function in the MATLAB software named 'awgn' to apply noise with a preset SNR to the AC magnetization of the sampling signal. A SNR during temperature measurement is set to 80 dB, a frequency of the excitation magnetic field is set to 1 kHz (low frequency point), 5 kHz (middle frequency point) and 10 kHz (high frequency point) for different purposes, and a temperature test range is between 300 K to 340 K.

Figure 5:
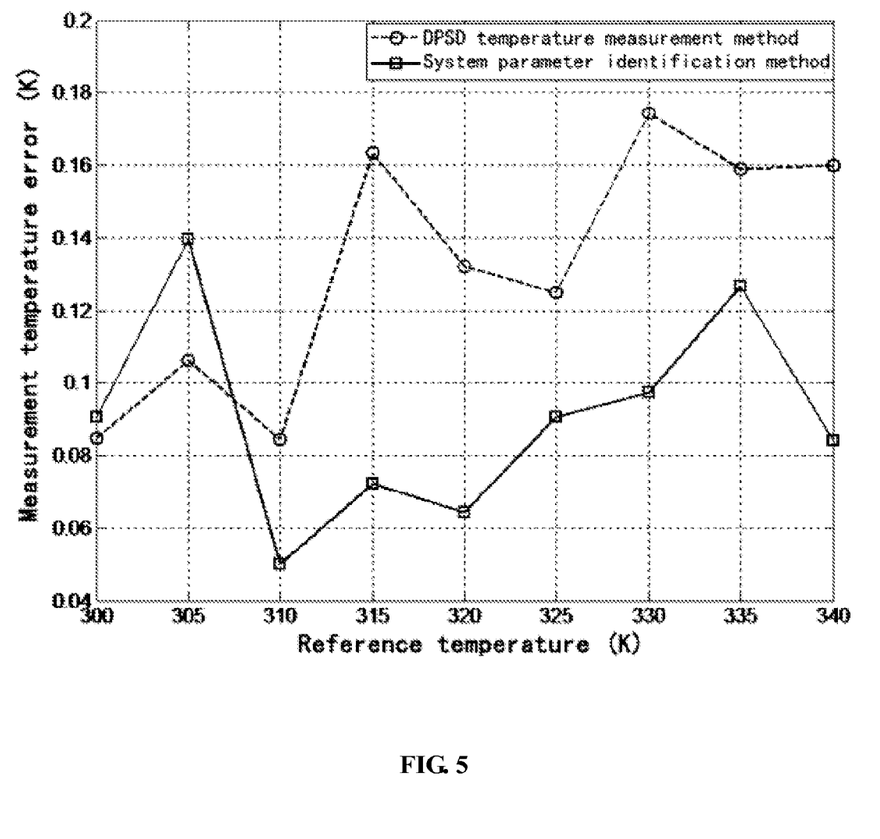
FIG. 5 illustrates temperature estimation errors obtained by measuring harmonics via the DPSD and the least square system parameter identification method at an excitation frequency of 1 kH.
Figure 6:
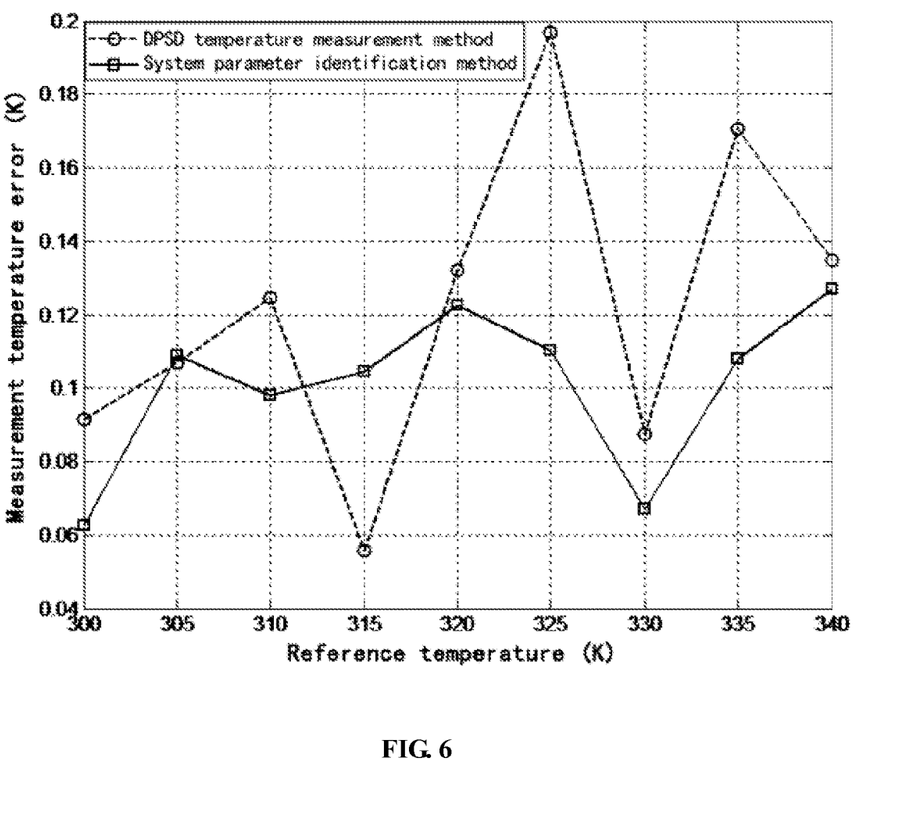
FIG. 6 illustrates temperature estimation errors obtained by measuring harmonics via the DPSD and the least square system parameter identification method at an excitation frequency of 5 kH.
Figure 7:
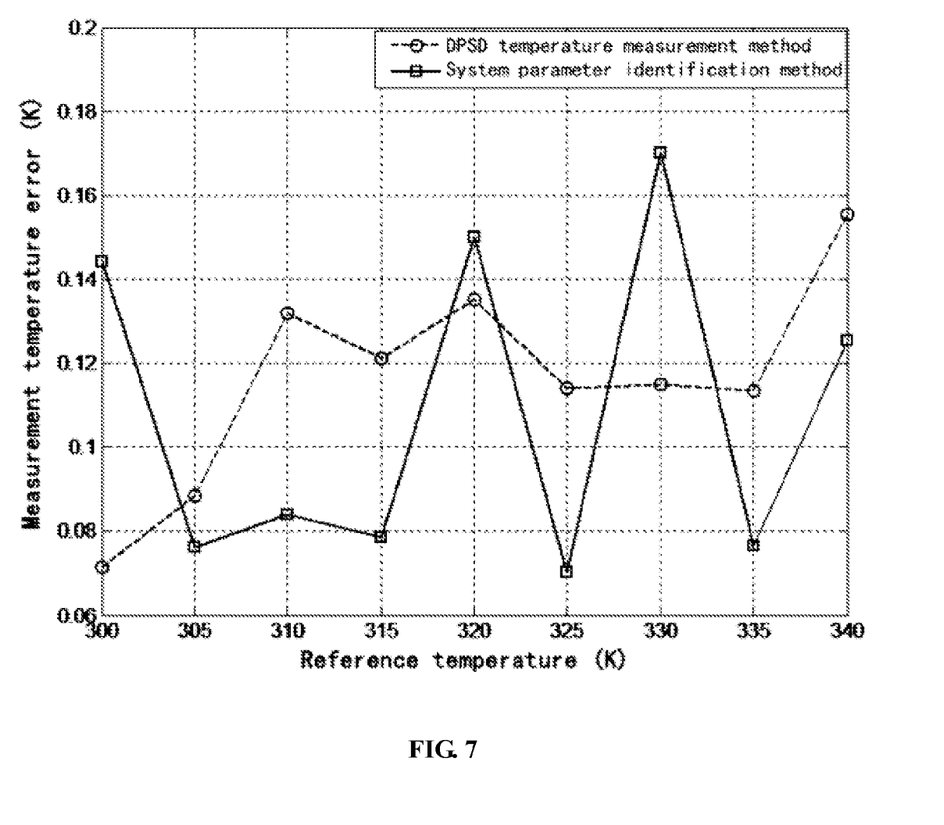
FIG. 7 illustrates temperature estimation errors obtained by measuring harmonics via the DPSD and the least square system parameter identification method at an excitation frequency of 10 kH.

To test accuracy of the temperature measurement method of the invention, the simulation uses the DPSD method and the least square system parameter identification method to test temperature estimation errors obtained from different harmonics in the AC magnetization of the magnetic nanoparticles. Meanwhile, to test repeatability of the method, an average temperature estimation error after ten times of repeated measurement is used. FIGS. 5 to 7 respectively illustrates an average temperature estimation error obtained by measuring harmonics via the DPSD and the least square system parameter identification method at an low excitation frequency of 1 kH, a middle excitation frequency of 5 kHz, and a high excitation frequency of 10 kHz.

2. Simulation Results

FIGS. 5 to 7 indicate no matter what frequency is used (a low frequency of 1 kHz, a middle frequency of 5 kHz, or a high frequency of 10 kHz), temperature estimation errors obtained by measuring harmonics via the DPSD and the least square system parameter identification method can be controlled below 0.2 K, and accuracy, stability and repeatability during measurement can be ensured. As a test SNR is set to 80 dB, the temperature measurement method of the invention features good noise resistance performance, and provides a new solution for accurate and fast noninvasive detection of organisms' temperature under highly complicated circumstances in the future.

While preferred embodiments of the invention have been described above, the invention is not limited to disclosure in the embodiments and the accompanying drawings. Any changes or modifications without departing from the spirit of the invention fall within the scope of the invention.

What is claimed is:

1. A method for in-vivo temperature measurement, comprising steps of:
   (1) positioning a magnetic nano agent at an area of a measured object;
   (2) applying an AC excitation magnetic field to said area;
   (3) collecting an AC magnetization signal of said magnetic nano agent under said AC excitation magnetic field using a coil sensor and processing the AC magnetization signal via a data acquisition card;
   (4) detecting amplitudes $C_1, C_3, \ldots, C_{2n-1}$ of odd harmonics of said AC magnetization signal, a number of said odd harmonics $n \geq 1$; and
   (5) calculating in-vivo temperature T according to equation $X=AY$,
   wherein said amplitudes of said odd harmonics form a column vector $$X = \begin{bmatrix} C_1 \\ C_3 \\ \vdots \\ C_{2n-1} \end{bmatrix};$$

wherein a coefficient matrix A is defined by expressing said AC magnetization signal via Langevin's function, and deducing an expression of said amplitudes of said odd harmonics from a Taylor series expansion of the Langevin's function, thereby obtaining said coefficient matrix $$A = \begin{bmatrix} \frac{M_s^2 H_0}{a_{1,1}k} & \frac{M_s^4 H_0^3}{a_{1,2}k^3} & \frac{M_s^6 H_0^5}{a_{1,3}k^5} & \cdots & \frac{M_s^{2m} H_0^{2m-1}}{a_{1,m}k^{2m-1}} \\ 0 & \frac{M_s^4 H_0^3}{a_{2,2}k^3} & \frac{M_s^6 H_0^5}{a_{2,3}k^5} & \cdots & \frac{M_s^{2m} H_0^{2m-1}}{a_{2,m}k^{2m-1}} \\ \vdots & \ddots & \ddots & \ddots & \vdots \\ \vdots & (0) & \ddots & \ddots & \frac{M_s^{2m} H_0^{2m-1}}{a_{n-1,m}k^{2m-1}} \\ 0 & \cdots & \cdots & \ddots & \frac{M_s^{2m} H_0^{2m-1}}{a_{n,m}k^{2m-1}} \end{bmatrix},$$

where $M_s$ is effective magnetic moment of a magnetic nanoparticle, k is a Boltzmann's constant, $H_0$ is an amplitude of said AC excitation magnetic field, $a_{u,v}$ is a coefficient of an element at the uth row and the vth column of said coefficient matrix A, where $u=1, 2, \ldots, n$, $v=1, 2, \ldots, m$, and m is a number of Taylor's expansion terms, and $m \geq n$;

wherein a related column vector Y of said in-vivo temperature is expressed as $$Y = \begin{bmatrix} \frac{N}{T} \\ \frac{N}{T^3} \\ \vdots \\ \frac{N}{T^{2m-1}} \end{bmatrix},$$

where T is said in-vivo temperature of said measured object, and N is magnetic nano concentration at said measured object.

2. The method for in-vivo temperature measurement of claim 1,
   wherein when the number of said Taylor's expansion terms m is equal to the number of said odd harmonics n, step (5) is performed by calculating said related column vector of said in-vivo temperature $Y=A^{-1}X$, and further said in-vivo temperature $T=^{2(q-p)}\sqrt{Y_p/Y_q}$, $1 \leq p<q \leq 2n-1$, where $Y_p$ and $Y_q$ respectively represents the $p^{th}$ and the $q^{th}$ element of said related column vector Y of said in-vivo temperature; and
   wherein when the number of said Taylor's expansion terms m is greater than the number of said odd harmonics n, step (5) is performed by performing least square fitting via $B=[N,T]^T$ as a variable and the relationship between said odd harmonics and said in-vivo temperature $X=AY$ as an objective function whereby determining said in-vivo temperature T.

3. The method for in-vivo temperature measurement of claim 1, wherein step (4) uses a digital phase-sensitive detection method to detect said amplitudes of said odd harmonics, and comprises sub-steps of:
   (a) sampling said AC magnetization signal M of said magnetic nano agent to obtain a discrete intensity signal M(i), where $1=1, 2 \ldots, L$, and L is the number of sampling points;
   (b) setting $j=1$;
   (c) calculating $f'=(2j-1)f$, where f is a frequency of said AC excitation magnetic field;
   (d) generating two orthogonal reference signals, and sampling said orthogonal reference signals to obtain two discrete sampling signals $R_1(i)$ and $R_2(i)$;
   (e) determining whether j is equal to 1, proceeding to step (g) if yes, and proceeding to step (f) otherwise;
   (f) filtering the $2j-3^{th}$ odd harmonic in said discrete intensity signal M(i);
   (g) performing mutual correlation calculation and mean filtering on the discrete sampling signal $R_1(i)$ and said discrete intensity signal M(i) to obtain a first component $S_{2j-1}$, performing mutual correlation calculation and mean filtering on the discrete sampling signal $R_2(i)$ and said discrete intensity signal M(i) to obtain a second component $O_{2j-1}$, and calculating an amplitude of a $2j-1^{th}$ odd harmonic $C_{2j-1}=2\sqrt{S_{2j-1}^2+O_{2j-1}^2}$; and
   (h) determining whether j is less than n, setting $j=j+1$ and retuning step (c) if yes, and ending otherwise.

4. The method for in-vivo temperature measurement of claim 1, wherein step (4) uses a least square system parameter identification method to detect said amplitudes of said odd harmonics, and comprises sub-steps of:
   sampling said AC magnetization signal M of said magnetic nano agent to obtain a discrete intensity signal M(i), where $1=1, 2 \ldots, L$, and L is the number of sampling points;

$$\text{assuming } Z = \begin{bmatrix} M(1) \\ M(2) \\ \vdots \\ M(L) \end{bmatrix} \text{ and}$$

-continued $$\varphi = \begin{bmatrix} \sin(\Omega) & \sin(3\Omega) & \ldots & \sin((2n-1)\Omega) \\ \sin(2\Omega) & \sin(6\Omega) & \ldots & \sin(2(2n-1)\Omega) \\ \vdots & \vdots & \ddots & \vdots \\ \sin(L\Omega) & \sin(3L\Omega) & \ldots & \sin(L(2n-1)\Omega) \end{bmatrix},$$

finding matrices $\phi$ and Z so that $J=[Z-\phi X]^T[Z-\phi X]$ is minimum by adjusting a sampling frequency, and determining said column vector $X=(\phi^T\phi)^{-1}\phi^T Z$ formed by said amplitudes $C_j$ of said odd harmonics, where a digital angular frequency $$\Omega = \frac{2\pi f}{f_s},$$

$f_s$ represents a sampling frequency, $\pi$ represents a circumference ratio, and a superscript T represents transpose.

5. The method for in-vivo temperature measurement of claim 1, wherein intensity of said AC excitation magnetic field ranges from 20 Oe to 1000 Oe, and a frequency of said AC excitation magnetic field ranges from 20 Hz to 20 kHz.

6. The method for in-vivo temperature measurement of claim 1, wherein the number of said odd harmonics n ranges from 2 to 4, and the number of said Taylor's expansion terms m ranges from 2 to 6.

7. An in-vivo temperature measurement system, comprising:
a first module configured to position a magnetic nano agent at an area of a measured object;
a second module configured to apply an AC excitation magnetic field to said area;
a third module configured to collect an AC magnetization signal of said magnetic nano agent under said AC excitation magnetic field in a digital form, the third module comprising a coil sensor and a data acquisition card;
a fourth module configured to detect amplitudes $C_1$, $C_3$, ..., $C_{2n-1}$ of odd harmonics of said AC magnetization signal, a number of said odd harmonics $n \geq 1$; and
a fifth module configured to calculate in-vivo temperature T according to equation X=AY,
wherein said amplitudes of said odd harmonics form a column vector $$X = \begin{bmatrix} C_1 \\ C_3 \\ \vdots \\ C_{2n-1} \end{bmatrix};$$

wherein a coefficient matrix A is defined by expressing said AC magnetization signal via Langevin's function, and deducing an expression of said amplitudes of said odd harmonics from a Taylor series expansion of the Langevin's function, thereby obtaining said coefficient matrix $$A = \begin{bmatrix} \frac{M_s^2 H_0}{a_{1,1}k} & \frac{M_s^4 H_0^3}{a_{1,2}k^3} & \frac{M_s^6 H_0^5}{a_{1,3}k^5} & \cdots & \frac{M_s^{2m}H_0^{2m-1}}{a_{1,m}k^{2m-1}} \\ 0 & \frac{M_s^4 H_0^3}{a_{2,2}k^3} & \frac{M_s^6 H_0^5}{a_{2,3}k^5} & \cdots & \frac{M_s^{2m}H_0^{2m-1}}{a_{2,m}k^{2m-1}} \\ \vdots & & \ddots & \ddots & \vdots \\ & (0) & & \ddots & \frac{M_s^{2m}H_0^{2m-1}}{a_{n-1,m}k^{2m-1}} \\ 0 & \cdots & \cdots & \ddots & \frac{M_s^{2m}H_0^{2m-1}}{a_{n,m}k^{2m-1}} \end{bmatrix},$$

where $M_s$ is effective magnetic moment of a magnetic nanoparticle, k is a Boltzmann's constant, $H_0$ is an amplitude of said AC excitation magnetic field, $a_{u,v}$ is a coefficient of an element at the uth row and the vth column of said coefficient matrix A, where u=1, 2, ..., n, v=1, 2 ..., m, and m is a number of Taylor's expansion terms, and m≥n;

wherein a related column vector Y of said in-vivo temperature is expressed as $$Y = \begin{bmatrix} \frac{N}{T} \\ \frac{N}{T^3} \\ \vdots \\ \frac{N}{T^{2m-1}} \end{bmatrix},$$

where T is said in-vivo temperature of said measured object, and N is magnetic nano concentration at said measured object.

8. The in-vivo temperature measurement system of claim 7, wherein said fifth module comprises:
a fifty-first sub-module configured to calculate said related column vector of said in-vivo temperature $Y=A^{-1}X$, and further said in-vivo temperature $T=^{2(q-p)}\sqrt{Y_p/Y_q}$, $1 \leq p < q \leq 2n-1$ when the number of said Taylor's expansion terms m is equal to the number of said odd harmonics n, where $Y_p$ and $Y_q$ respectively represents the $p^{th}$ and the $q^{th}$ element of said related column vector Y of said in-vivo temperature; and
a fifty-second sub-module configured to perform least square fitting via $B=[N,T]^T$ as a variable and the relationship between said odd harmonics and said in-vivo temperature X=AY as an objective function whereby determining said in-vivo temperature T when the number of said Taylor's expansion terms m is greater than the number of said odd harmonics n.

9. The in-vivo temperature measurement system of claim 7, wherein said fourth module is configured to use a digital phase-sensitive detection method to detect said amplitudes of said odd harmonics, and comprises:
a forty-first sub-module configured to sample said AC magnetization signal M of said magnetic nano agent to obtain a discrete intensity signal M(i), where i=1, 2 ..., L, and L is the number of sampling points;
a forty-second sub-module configured to set j=1;
a forty-third sub-module configured to calculate f'=(2j-1)f where f is a frequency of said AC excitation magnetic field;
a forty-fourth sub-module configured to generate two orthogonal reference signals, and to sample said orthogonal reference signals to obtain two discrete sampling signals $R_1(i)$ and $R_2(i)$;

a forty-fifth sub-module configured to determine whether j is equal to 1, to proceed to step (g) if yes, and to proceed to step (f) otherwise;

a forty-sixth sub-module configured to filter the $2j-3^{th}$ odd harmonic in said discrete intensity signal M(i);

a forty-seventh sub-module configured to perform mutual correlation calculation and mean filtering on the discrete sampling signal $R_1(i)$ and said discrete intensity signal M(i) to obtain a first component $S_{2j-1}$, to perform mutual correlation calculation and mean filtering on the discrete sampling signal $R_2(i)$ and said discrete intensity signal M(i) to obtain a second component $O_{2j-1}$ and to calculate an amplitude of a $2j-1^{th}$ odd harmonic $C_{2j-1}=2\sqrt{S_{2j-1}^2+O_{2j-1}^2}$; and a forty-eighth sub-module configured to determine whether j is less than n, to set j=j+1 and return step (c) if yes, and to end otherwise.

10. The in-vivo temperature measurement system of claim 7, wherein said fourth module is configured to use a least square system parameter identification method to detect said amplitudes of said odd harmonics, wherein said fourth module is configured to sample said AC magnetization signal M of said magnetic nano agent to obtain a discrete intensity signal M(i) where i=1, 2 ..., L, and L is the number of sampling points;

wherein said fourth module is configured to assume $$Z = \begin{bmatrix} M(1) \\ M(2) \\ \vdots \\ M(L) \end{bmatrix} \text{ and }$$

$$\varphi = \begin{bmatrix} \sin(\Omega) & \sin(3\Omega) & \ldots & \sin((2n-1)\Omega) \\ \sin(2\Omega) & \sin(6\Omega) & \ldots & \sin(2(2n-1)\Omega) \\ \vdots & \vdots & \ddots & \vdots \\ \sin(L\Omega) & \sin(3L\Omega) & \ldots & \sin(L(2n-1)\Omega) \end{bmatrix},$$

wherein the fourth module is configured to adjust a sampling frequency to find matrices $\varphi$ and Z so that $J=[Z-\varphi X]^T[Z-\varphi X]$ is the minimum, and wherein said fourth module is configured to determine said column vector $X=(\varphi^T\varphi)^{-1}\varphi^T Z$ formed by said amplitudes $C_j$ of said odd harmonics, where a digital angular frequency $$\Omega = \frac{2\pi f}{f_s},$$

$f_s$ represents a sampling frequency, $\pi$ represents a circumference ratio, and a superscript T represents transpose.

* * * * *